(12) United States Patent
O'Sullivan et al.

(10) Patent No.: US 11,397,126 B2
(45) Date of Patent: Jul. 26, 2022

(54) SYSTEM AND METHOD FOR GROUNDED HIGH VOLTAGE LEAK DETECTION

(71) Applicant: Packaging Technologies and Inspection, LLC, Hawthorne, NY (US)

(72) Inventors: Andrew William O'Sullivan, Brooklyn, NY (US); Heinz Wolf, Hackettstown, NJ (US); Ross Treloar, Tuckahoe, NY (US); Sandipan Saha, Yonkers, NY (US)

(73) Assignee: Packaging Technologies and Inspection, LLC, Hawthorne, NY (US)

( * ) Notice: Subject to any disclaimer, the term of this patent is extended or adjusted under 35 U.S.C. 154(b) by 290 days.

(21) Appl. No.: 16/796,396

(22) Filed: Feb. 20, 2020

(65) Prior Publication Data

US 2021/0262889 A1    Aug. 26, 2021

(51) Int. Cl.
| | |
|---|---|
| *G01M 3/40* | (2006.01) |
| *G01R 31/16* | (2006.01) |
| *G01M 3/16* | (2006.01) |
| *G01N 33/00* | (2006.01) |

(52) U.S. Cl.
CPC .............. *G01M 3/40* (2013.01); *G01M 3/16* (2013.01); *G01R 31/16* (2013.01); *G01N 2033/0081* (2013.01)

(58) Field of Classification Search
CPC .......... G01M 3/40; G01M 3/16; G01R 31/16; G01N 2033/0081
See application file for complete search history.

(56) References Cited

U.S. PATENT DOCUMENTS

| | | | |
|---|---|---|---|
| 4,125,805 A | 11/1978 | Nagamatsu et al. | |
| 2014/0009169 A1* | 1/2014 | Langois | G01M 3/40 324/557 |

FOREIGN PATENT DOCUMENTS

| | | | | |
|---|---|---|---|---|
| CN | 112946428 A | * | 6/2021 | |
| JP | 2011064556 A | * | 3/2011 | |
| WO | 2004/051255 A1 | | 6/2004 | |
| WO | WO-2004051255 A1 | * | 6/2004 | G01N 27/205 |
| WO | 2017/136007 A1 | | 8/2017 | |
| WO | WO-2017136007 A1 | * | 8/2017 | G01M 3/16 |

(Continued)

OTHER PUBLICATIONS

"Common static electricity problems and remedies: a series of brief articles", AlphaLab Inc., www.alphalabinc.com/common-static-problems, last accessed Oct. 24, 2019.

(Continued)

*Primary Examiner* — Peter J Macchiarolo
*Assistant Examiner* — Fatemeh Esfandiari Nia
(74) *Attorney, Agent, or Firm* — Benesch, Friedlander, Coplan & Aronoff LLP (57) ABSTRACT

A leak detection system includes a high voltage leak detection (HVLD) testing system configured to inspect a package using a HVLD apparatus that includes an inspection electrode and a detection electrode. The leak detection system includes a grounding system that includes a grounding element. The grounding system is configured to remove, significantly reduce, or conduct away electric charge accumulation on the package. The leak detection system also includes a controller configured to operate and coordinate the operation of the grounding system with the operation of the HVLD testing system.

19 Claims, 5 Drawing Sheets

(56) References Cited

FOREIGN PATENT DOCUMENTS

WO        2019/157036 A1    8/2019
WO    WO-2019157036 A1 *   8/2019  ............... A61J 1/00

OTHER PUBLICATIONS

International Search Report and Written Opinion in International Application No. PCT/US20/26410, dated Jun. 26, 2020 (30 pages).

\* cited by examiner

SYSTEM AND METHOD FOR GROUNDED HIGH VOLTAGE LEAK DETECTION

FIELD

The present disclosure relates to systems and methods for high voltage leak detection.

BACKGROUND

High voltage leak detection (HVLD) is one of the emerging technologies for inspecting leakage. HVLD operates by applying a high voltage potential to an electrically conductive substance inside non-conductive package or container. Defects are identified when the electrical discharges are detected between the substance inside the package and HVLD electrodes. For example, a HVLD testing process may include of a set of electrodes scanning a sealed package containing a liquid. The presence of a current flow or voltage between the set of electrodes indicates a breach of the package closure, which may be attributed by the presence of a crack, a leak, a pin hole, or a seal imperfection.

SUMMARY

In one embodiment, a leak detection system includes a high voltage leak detection (HVLD) testing system configured to inspect a package using a HVLD apparatus that includes an inspection electrode and a detection electrode. The leak detection system includes a grounding system that includes a grounding element. The grounding system is configured to remove, significantly reduce, or conduct away electric charge accumulation on the package. The leak detection system also includes a controller configured to operate and coordinate the operation of the grounding system with the operation of the HVLD testing system.

In another embodiment, a grounding system for high voltage leak detection (HVLD) inspection includes a grounding system that includes a grounding element. The grounding system is configured to be coupled to a HVLD testing system that is configured to inspect a package using a HVLD apparatus. The HVLD apparatus includes an inspection electrode and a detection electrode. The grounding element is also configured to be positioned near or contact the package to remove, significantly reduce, or conduct away electric charge accumulation on the package.

In another embodiment, a method for high voltage leak detection (HVLD) inspection includes grounding a package by positioning at least one grounding element near or contact the package to remove, significantly reduce, or conduct away electric charge accumulation on the package. The method also includes performing HVLD inspection on the package using a HVLD testing system.

The summary is provided merely for purposes of summarizing some example embodiments so as to provide a basic understanding of some aspects of the disclosure. Accordingly, it will be appreciated that the above-described examples should not be construed to narrow the scope of the disclosure in any way. Other examples, embodiments, aspects, and advantages will become apparent from the following detailed description taken in conjunction with the accompanying drawings.

DETAILED DESCRIPTION

The present disclosure is not limited in terms of the particular embodiments described in this application, which are intended as illustrations of various aspects only. Many modifications and variations can be made without departing from the scope of the invention, as will be apparent to those skilled in the art. Functionally equivalent methods within the scope of the disclosure, in addition to those enumerated herein, will be apparent to those skilled in the art from the following descriptions. Such modifications and variations are intended to fall within the scope of the appended claims. The terminology used herein is for the purpose of describing particular embodiments only, and is not intended to be limiting.

The present disclosure is related to systems and methods for high voltage leakage detection (HVLD). In particular, the systems and methods disclosed herein seek to reduce signal noise and/or to improve the reliability of HVLD detection. HVLD operates by applying a high voltage potential to an electrically conductive substance inside non-conductive package or container. The presence of a current flow or voltage between the inspecting electrodes can indicate a breach of the package closure, which may be attributed to the presence of a crack, a leak, a pin hole, or a seal imperfection. However, it may be challenging to produce reliable and consistent results. In particular, when HVLD inspection is performed on a non-conductive package, the results may become less consistent as the inspection proceeds and/or when subsequent inspections are performed on the same package. The inconsistent results may lead to inaccurate and/or unreliable leakage detection. In an example, when HVLD inspection is performed on an intravenous (IV) bag, the results from the first-time inspection are acceptable but the results from the subsequent inspections (e.g., the second-time inspection, third-time inspection, and so forth) may be inconsistent. In particular, the HVLD test results are often masked by signal noises with a lower signal-to-noise ratio (SNR) in the subsequent inspections. SNR is a measure used in data analysis that compares the level of the desired signal to the level of background noise, and SNR is defined as the ratio of the signal power to the noise power (e.g., a ratio higher than 1:1 indicates more signal than noise).

The systems and methods described herein may include a system grounding the package before, during, and/or after the HVLD inspection. As the package is grounded to remove the static charge accumulated during the HVLD inspection, signal noise is substantially removed or significantly reduced, leading to an enhanced SNR. The enhanced SNR may improve the reliability and/or accuracy of the HVLD inspection.

Figure 1:
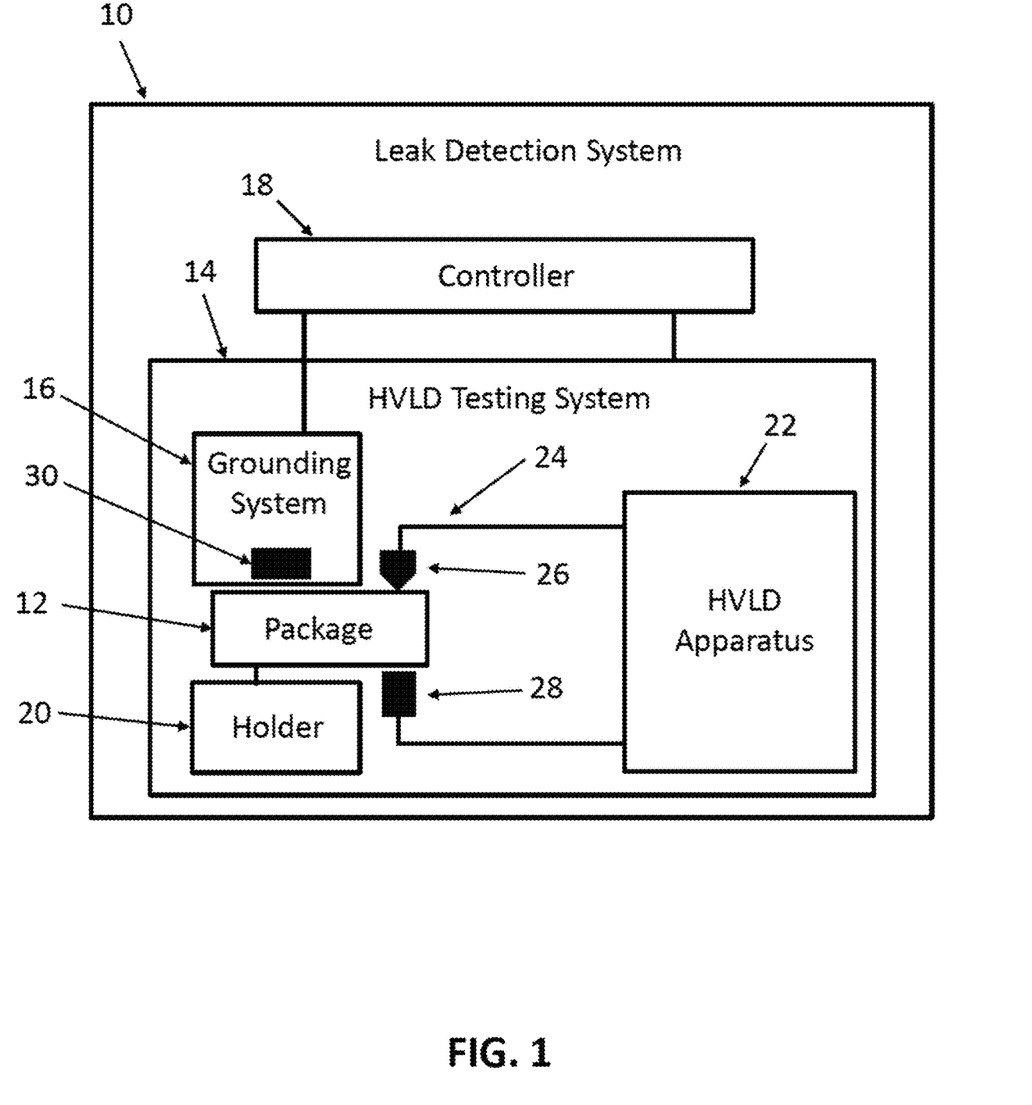
FIG. 1 shows a diagram of a leak detection system including a HVLD testing system and a grounding system.

FIG. 1 shows a diagram of an example leak detection system 10 configured to inspect a package 12 in accordance with an embodiment of the present disclosure. In the illustrated example, the leak detection system 10 includes a HVLD testing system 14, a grounding system 16, and a controller 18 operatively and communicatively coupled to the HVLD testing system 14 and the grounding system 16. The package 12 may have any suitable shapes and may be made of any suitable non-conductive material (e.g., polymer, plastic, glass, ceramic, composites, etc.) to contain a liquid within the package 12. For example, the package 12 may be an IV bag, a syringe, a vial, etc.

In the illustrated example, the HVLD testing system 14 includes a holder 20 configured to retain and/or rotate the package 12. For example, the holder 20 may include one or more rollers or rotational rests (e.g., one or more rods) configured to receive and/or rotate the package 12. The HVLD testing system 14 may include a HVLD apparatus 22 configured to perform HVLD inspection. The HVLD apparatus 22 may be any suitable leak detection circuit or apparatus to perform HVLD inspection on the package 12. For example, the HVLD apparatus 22 may be a testing system or apparatus manufactured by Packaging Technologies and Inspection, LLC. The HVLD apparatus 14 may include a scanner 24 (e.g., E-Scan™, model 655) that includes an inspection electrode 26 and a detection electrode 28 to inspect the package 12. The inspection electrode 26 and the detection electrode 28 are configured to be positioned near and/or contact opposite sides of the package 12 and scan across the package 12 to inspect the package 12.

In the illustrated example, the grounding system 16 may include a grounding element 30 that is configured to be positioned near and/or contact the surface (e.g., outer surface) of the package 12 to remove, significantly reduce, or conduct away electric charge accumulation (e.g., static charge) on the package 12. The grounding element 30 may be configured to scan the surface of the package 12. The grounding element 30 may be configured to move together with the inspection electrode 26 and/or the detection electrode 28 to scan the surface of the package 12. The grounding element 30 may have any suitable shapes (e.g., brush, probe, pin, roller, rotational rest, rod, etc.) and may be made of any suitable electrically conductive or semi-conductive material (e.g., metal, alloy, conductive or semi-conductive polymer, etc.).

The controller 18 may be configured to operate and coordinate the operation of the grounding system 16 with the operation of the HVLD testing system 14. The controller 18 may include any suitable processer (e.g., microprocessor, MOSFET, IGBT, etc.) and memory. The controller 18 may include any suitable user interface and/or display to allow a user to program and/or provide inputs to control the operation of the HVLD testing system 14 and/or the operation of the grounding system 16. The controller 18 may receive instructions from a user or may be pre-programmed to inspect the package 12 following certain procedures or predetermined procedures.

Figure 2:
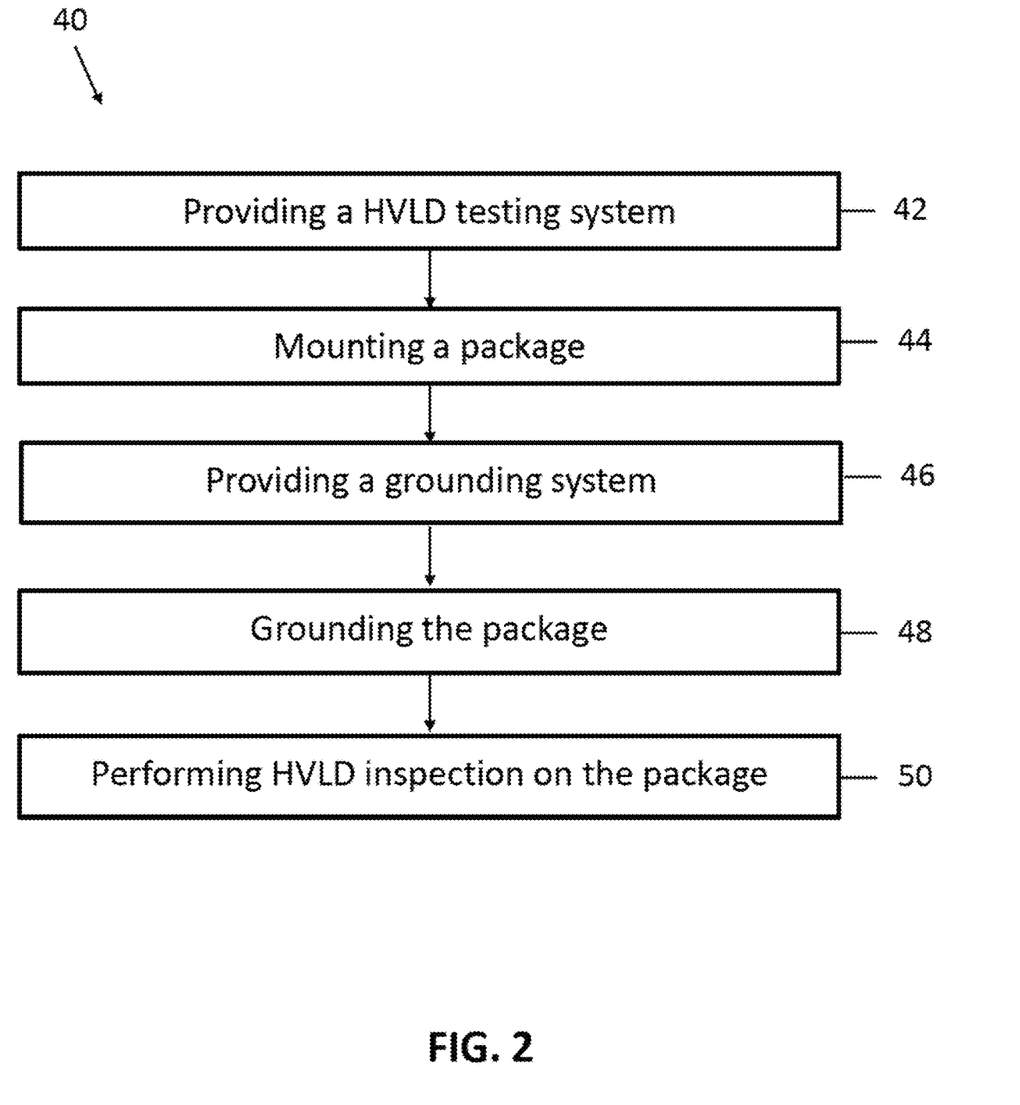
FIG. 2 shows an example method of HVLD inspection using the leak detection system of FIG. 1.

FIG. 2 shows a method 40 for inspecting a package using the leak detection system 10. The steps discussed herein may be controlled and executed by the controller 18. The method 40 may include (step 42) providing a HVLD testing system configured to inspect a package using a scanner comprising an inspection electrode and a detection electrode. For example, step 42 may include providing the HVLD testing system 14 or the HVLD apparatus 22.

The method 100 may include (step 44) mounting a package (e.g., the package 12) and (step 46) providing a grounding system (e.g., the grounding system 16). Step 44 may include mounting the package 12 on the holder 22 of the HVLD testing system 14. Step 46 may include orienting and/or positioning the grounding system 16 (in particular the grounding element 30) in proximity of the package 12 and the HVLD apparatus 22 to allow inspection and grounding of the package 12. Step 46 may include configuring the controller 18 to control and coordinate the operation of the grounding system 16 with the operation of the HVLD testing system 14.

The method 40 may include (step 48) grounding the package (e.g., the package 12) by positioning at least one grounding element near or contact the package to remove, significantly reduce, or conduct away electric charge accumulation on the package. The method 40 may include (step 50) performing HVLD inspection on the package. Step 50 may include using the HVLD testing system 14 to inspect the package 12 (e.g., using the HVLD apparatus 22 to scan the package 12).

Figure 3:
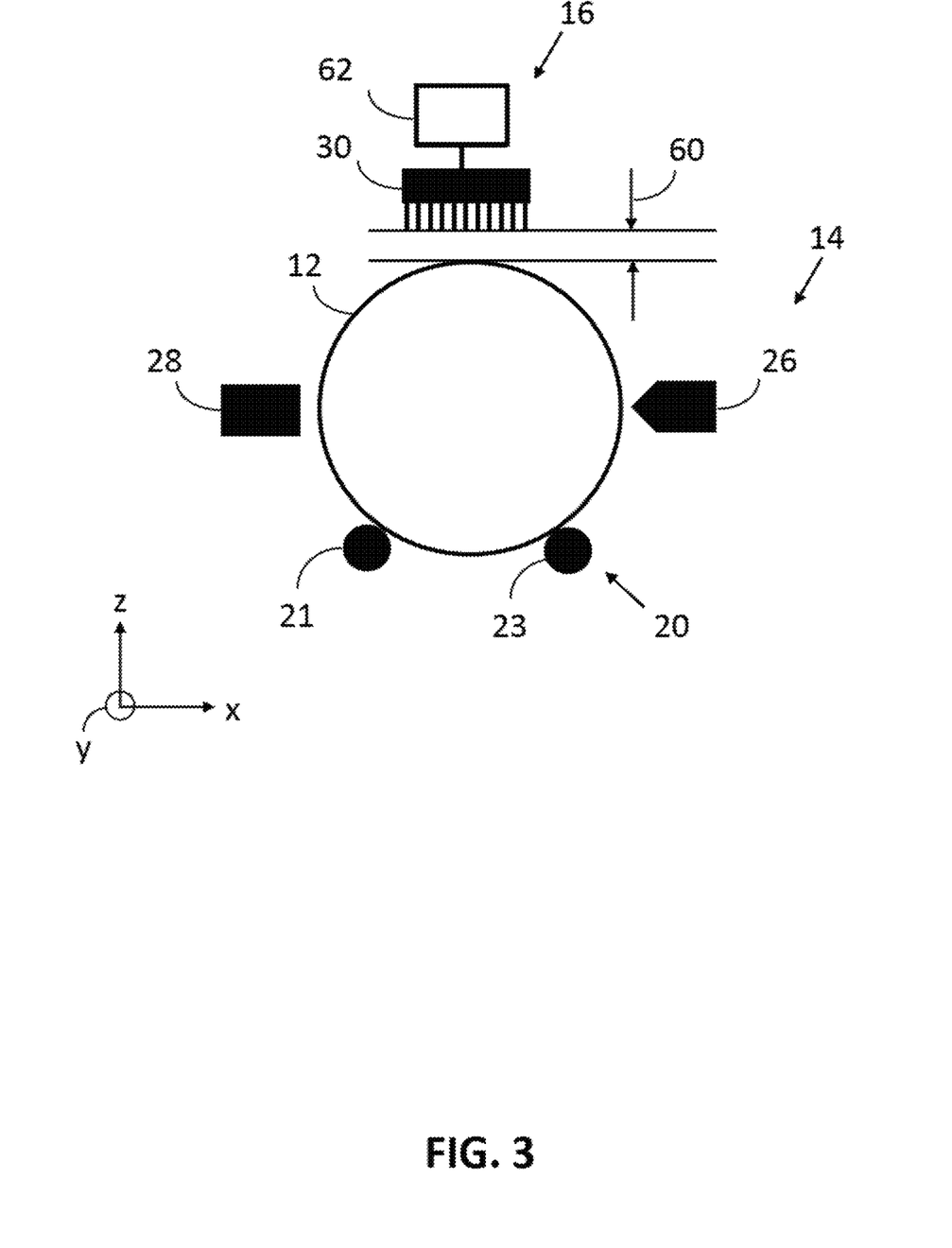
FIG. 3 shows a front view of a partial schematic of the leak detection system of FIG. 1 including the grounding system configured to ground a package before, during, and/or after inspecting the package.

FIG. 3 show a schematic illustrating example processes of step 48. For example, step 48 may include moving the grounding element 30 to a position between the inspection electrode 26 and the detection electrode 28. Step 48 may include moving the grounding element 30 to an effective distance 60 from the surface of the package 12 to ground the package 12. The effective distance 60 may be any suitable distances to effectively ground the package 12. The effective distance 60 may depend on many factors, e.g., the amount of charge accumulated, the material of the package 12, the material of the grounding element 30, the shape of the grounding element 30, the ambient environment (e.g., humidity), etc. In some embodiments, the effective distance 60 may be about 0.1 millimeter (mm) to about 6 mm, about 0.1 mm to about 5 mm, or about 0.1 mm to about 3 mm. Step 48 may include moving the grounding element 30 to contact (e.g., the effective distance 60 is zero) the package 12. The grounding element 30 may be coupled to an actuator 62 which is configured to move the grounding element 30 in the x-direction, y-direction, z-direction, or any combination thereof. The actuator 62 may be any suitable types of actuator, including but are not limited to, a pneumatic actuator, a solenoid actuator, and a lead screw.

In some embodiments, the package 12 may be received by the holder 20 that includes one or more rollers or rotational rests 21 and 23 (e.g., rods, rotatable rods). The rollers or rotational rests 21 and 23 are configured to contact and/or rotate the package 12. In this embodiment, the grounding element 30 may include the one or more rollers or rotational rests 21 and 23, and at least one of the rollers or rotational rests 21 and 23 are made of electrically conductive or semi-conductive material (e.g., metal, alloy, conductive or semi-conductive polymer, etc.). The one or more rollers or rotational rests 21 and 23 function as the grounding element 30 to ground the package 12 when the package 12 contacts or sits on the one or more rollers or rotational rests 21 and 23. In one embodiment, at least one of the rollers or rotational rests 21 and 23 are made of titanium.

Step 48 may be performed either before, during, or after performing a HVLD inspection. In an embodiment that the package 12 is grounded during performing a HVLD inspection, inspecting the package 12 using the HVLD testing system 14 and grounding the package 12 are performed at the same time (e.g., coordinated using the controller 18). In this embodiment, step 48 includes moving the grounding element 30 along with the inspection electrode 26 and/or the detection electrode 28 such that the grounding element 30 is between the inspection electrode 26 and the detection electrode 28 during the HVLD inspection and the grounding element 30 does not interfere with the scanning of the inspection electrode 26 and the detection electrode 28. For example, while the inspection electrode 26 and/or the detection electrode 28 move in the y-direction to scan across the surface of the package 12, the grounding element 30 also movies in the y-direction at a suitable speed to maintain its position between the inspection electrode 26 and the detection electrode 28. The grounding element 30 is configured to maintain contact with the package 12 or maintain the effective distance 60 from the package 12 while moving along with the inspection electrode 26 and/or the detection electrode 28.

In an embodiment that the package 12 is grounded before performing a HVLD inspection, step 50 is performed after step 48. For example, step 50 is performed within a time period that the grounding effect is effective, e.g., step 50 is performed immediately after step 48, within a few minutes after step 48, or within a few seconds after step 48, etc. The grounding element 30 is positioned within the effective distance 60 from the surface of the package 12 or in direct contact with the package 12 to ground the package 12. The HVLD inspection proceeds after the package 12 has been grounded.

In an embodiment that the package 12 is grounded after preforming a HVLD inspection, step 48 is performed after step 50. For example, within a few minutes or a few seconds after the package 12 is inspected using the HVLD testing system 14, the grounding element 30 is positioned within the effective distance 60 from the surface of the package 12 or in direct contact with the package 12 to ground the package 12 and to prepare the package for a subsequent HVLD inspection.

The leak detection system 10 disclosed herein with the grounding system 16 is configured to remove the static charge accumulated on the inspection sample or package to reduce signal noise. As the signal noise is substantially removed or significantly reduced, the SNR can be enhanced, leading to improved reliability and/or accuracy of the HVLD inspection. In some embodiments, using the leak detection system 10 disclosed herein, the SNR may be increased by at least 10%, at least 20%, at least 30%, at least 40%, or at least 50%, compared to HVLD inspections obtained using a HVLD system without a grounding system. In some embodiments, using the leak detection system 10 disclosed herein, the SNR may be greater than about 4, greater than about 5, or greater than about 6.

EXAMPLES

Figure 4:
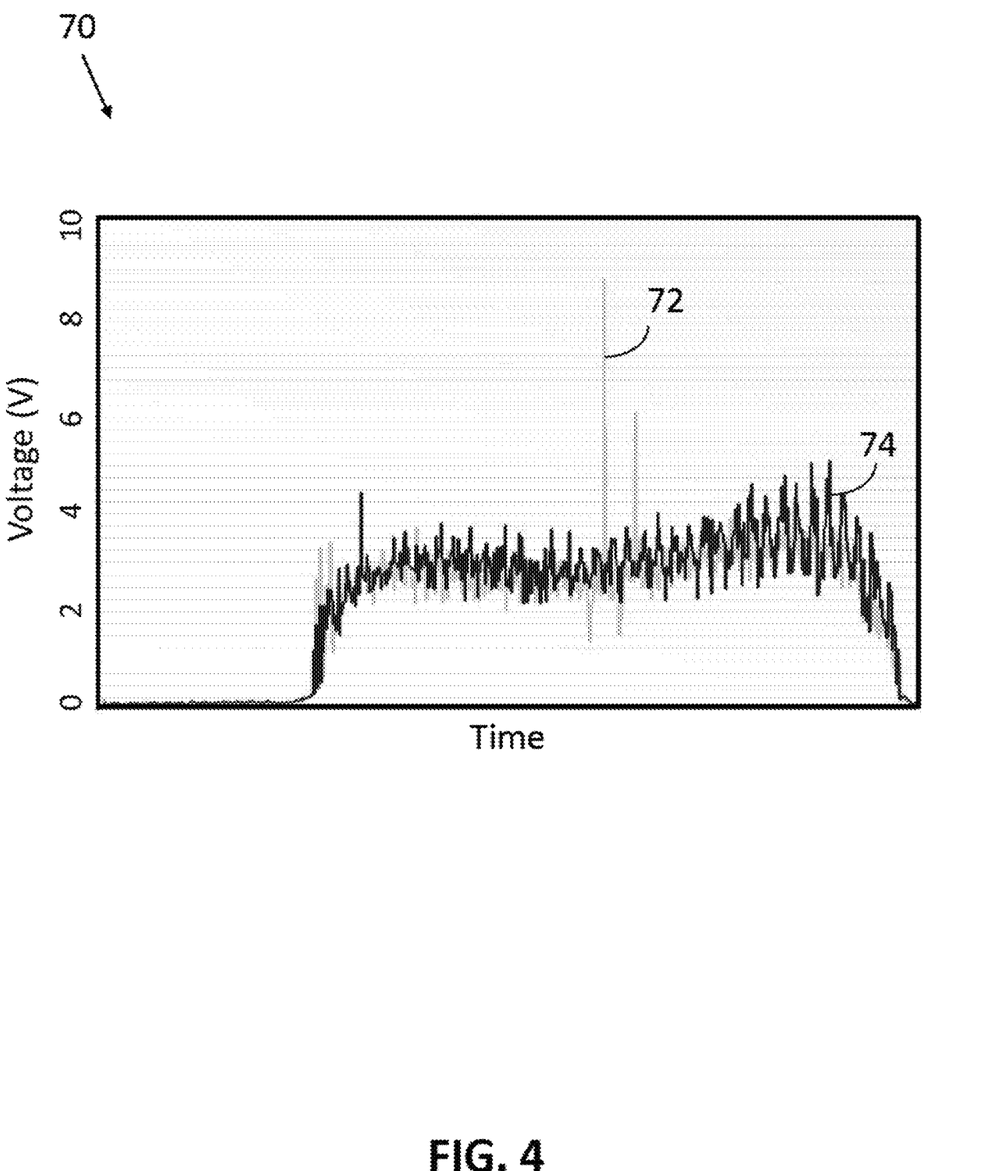
FIG. 4 shows an example HVLD inspection result from an ungrounded package inspected using the leak detection system of FIG. 1.
Figure 5:
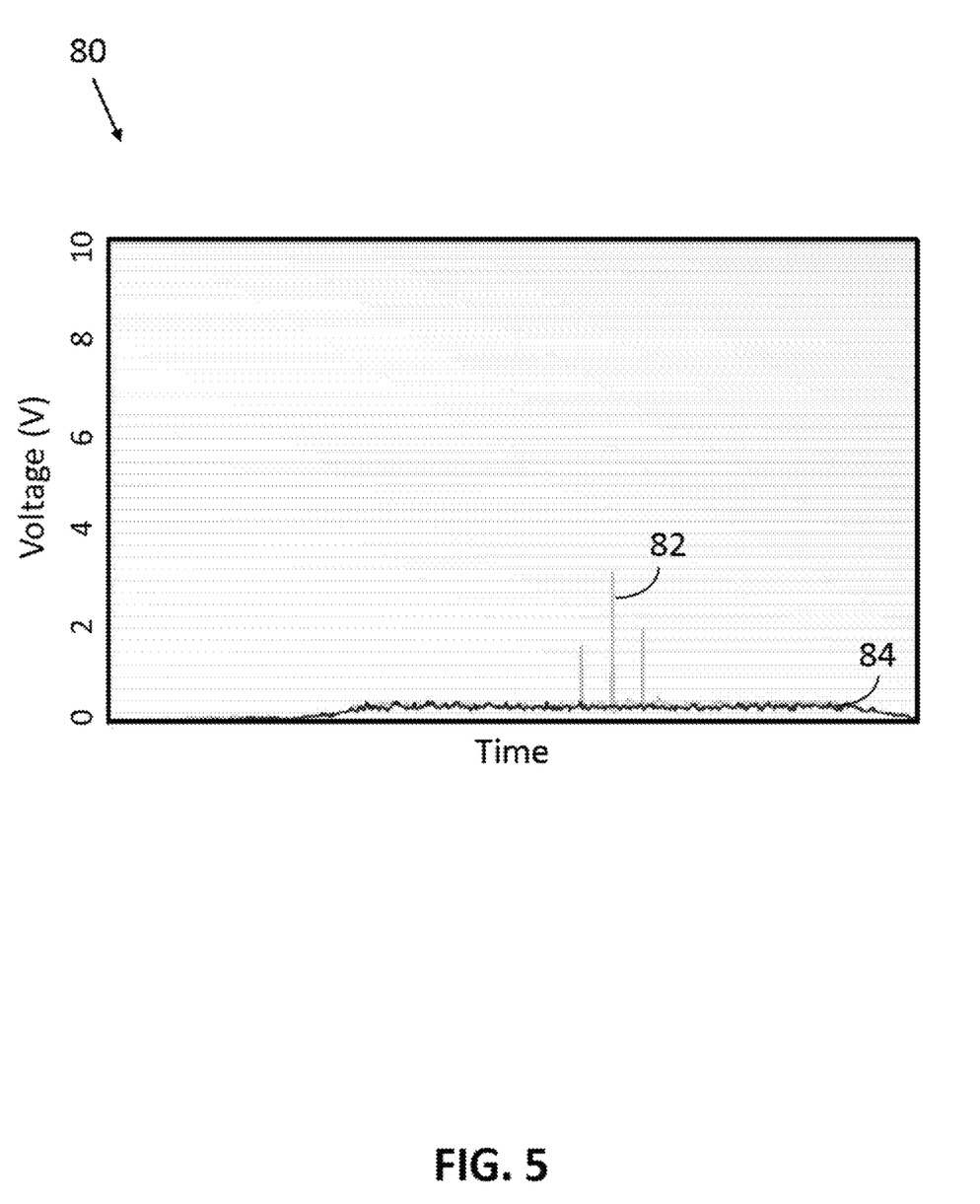
FIG. 5 shows an example HVLD inspection result from a grounded package inspected using the leak detection system of FIG. 1.

Tables 1 and 2 and FIGS. 4 and 5 show example experimental data illustrating that the SNR of the HVLD inspection is improved using the systems and methods described herein. SNR is a measure used in data analysis that compares the level of the desired signal to the level of background noise, and SNR is defined as the ratio of the signal power to the noise power (e.g., a ratio higher than 1:1 indicates more signal than noise). The signal power is calculated as the difference between the minimum value of a positive control and the mean value of the negative control. The noise power is calculated as three times the standard deviation of the negative control. Therefore, SNR may be calculated as SNR=[(Min. positive)−(Avg. negative)]/[(Std. negative)×3].

Experimental Procedure: A package of a 400 milliliter (mL) vial filled with a 100 microsiemens (μS) solution was subjected to a HVLD inspection using the systems (e.g., the leak detection system 10) and methods (e.g., the method 40) disclosed herein with and without a grounding process. The grounding process was performed during the HVLD inspection. In particular, a ground brush (e.g., the grounding element 30) touched the outer surface of the vial throughout the HVLD inspection while the inspection electrode (e.g., the inspection electrode 26) and the detection electrode (e.g., the detection electrode 28) moved across the length of the vial. The ground brush was configured to remove surface charge from the vial and allow the signal corresponding to a defect to be clearly detected (e.g., distinguishable from the noise). It should be noted that although in the illustrated experiment, the grounding process was performed during the HVLD inspection, we may expect similar effects if the grounding process was performed before the HVLD inspection.

The experimental results from the ungrounded HVLD inspection are shown in Table 1 and FIG. 4, and that of the grounded HVLD inspection are shown in Table 2 and FIG. 5.

TABLE 1

Ungrounded 400 mL Vial

|  | Avg | Std | Min | Max | Avg + 6 * Std | SNR |
|---|---|---|---|---|---|---|
| Negative | 5.64 | 0.20 | 5.07 | 6.05 | 6.85 | 4 |
| Positive | 9.86 | 0.38 | 8.01 | 10.00 | — | — |

TABLE 2

Grounded 400 mL Vial

|  | Avg | Std | Min | Max | Avg + 6 * Std | SNR |
|---|---|---|---|---|---|---|
| Negative | 0.46 | 0.02 | 0.42 | 0.51 | 0.59 | 6 |
| Positive | 1.09 | 0.11 | 0.85 | 1.37 | — | — |

FIG. 4 shows a plot 70 of the ungrounded HVLD inspection results. In the plot 70, the x-axis indicates time and the y-axis indicates voltage in volt (V). Data series 72 and 74 correspond to a positive control and a negative control, respectively, and the corresponding average (Avg), standard deviation (Std), minimum (Min), maximum (Max), (Avg+6*Std), and SNR values of the data series are summarized in Table 1. FIG. 5 shows a plot 80 of the grounded HVLD inspection results. In the plot 80, the x-axis indicates time and the y-axis indicates voltage in volt (V). Data series 82 and 84 correspond to a positive control and a negative control, respectively, and the average (Avg), standard deviation (Std), minimum (Min), maximum (Max), (Avg+6*Std), and SNR values of the data series are summarized in Table 1.

With reference to FIGS. 4 and 5, the HVLD inspection data (FIG. 5) obtained from the grounded vial indicate a clearer defect detection than that obtained from the ungrounded vial (FIG. 4). For example, the contrast or distinction between the positive control and negative control is more distinguishable in FIG. 5 than in FIG. 4. Furthermore, with reference to Tables 1 and 2, the SNR of the data from the ungrounded HVLD inspection is only 4, whereas the SNR of the data from the grounded HVLD inspection is significantly increased by 50%, from 4 to 6. These results indicate that by grounding the package using the systems and methods disclosed herein, the signal noise can be reduced and the SNR be enhanced, leading to more reliable and consistent HVLD inspection.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The invention claimed is:

1. A leak detection system, comprising:
a high voltage leak detection (HVLD) testing system comprising an inspection electrode and a detection electrode, wherein the inspection electrode and/or the detection electrode are configured to scan a surface of the package to inspect the package;
a grounding system comprising a grounding element, wherein the grounding system is configured to remove, significantly reduce, or conduct away electric charge accumulation on the package by moving the grounding element to an operative position within a range of effective distance from a surface of the package; and
a controller configured to predetermine the range of effective distance based on one or more factors comprising material of the grounding element, shape of the grounding element, ambient environment, and humidity, and the controller is further configured to operate and coordinate the operation of the grounding system with the operation of the HVLD testing system.

2. The leak detection system of claim 1, wherein the grounding system is configured to ground the package before, during, and/or after the HVLD inspection of the package.

3. The leak detection system of claim 1, wherein the controller is configured to move the grounding element to the operative position within the range of effective distance including an effective distance equal to zero.

4. The leak detection system of claim 1, wherein the grounding system is configured to move the grounding element to the operative position between the inspection electrode and the detection electrode to ground the package.

5. The leak detection system of claim 1, wherein the controller is configured to move the grounding element together with the inspection element and/or the detection element such that the grounding element is between the inspection element and the detection element to ground the package.

6. The leak detection system of claim 1, wherein the grounding element is semi-conductive.

7. The leak detection system of claim 1, wherein the grounding element comprises a brush.

8. The leak detection system of claim 1, wherein the grounding system is configured to move the grounding element to the operative position to increase a signal-to-noise-ratio (SNR) of the HVLD inspection by at least 10%, at least 20%, at least 30%, at least 40%, or at least 50%, compared to a HVLD inspection that is not grounded by the grounding system.

9. The leak detection system of claim 8, wherein the signal-to-noise-ratio (SNR) of the HVLD inspection is greater than about 4, greater than about 5, or greater than about 6.

10. The leak detection system of claim 1, wherein the grounding element further comprises rollers to retain, rotate, and ground the package.

11. A method of using the system of claim 1 for high voltage leak detection (HVLD) inspection, comprising: predetermining the range of effective distance from the grounding element to the surface of the package based on one or more factors comprising material of the grounding element, shape of the grounding element, ambient environment, and humidity; grounding the package by moving the grounding element within the range of effective distance to remove, significantly reduce, or conduct away electric charge accumulation on the package; and performing HVLD inspection on the package using the HVLD testing system by scanning the surface of the package using the inspection electrode and the detection electrode.

12. The method of claim 11, comprising moving the grounding element to the range of effective distance including an effective distance equal to zero.

13. The method of claim 11, comprising moving the grounding element to an operative position between the inspection electrode and the detection electrode of the HVLD testing system and within the effective distance from the surface of the package to ground the package.

14. The method of claim 11, comprising moving the grounding element along with the inspection electrode and/or the detection electrode of the HVLD testing system such that the grounding element is between the inspection electrode and the detection electrode during the HVLD inspection.

15. The method of claim 11, comprising grounding the package before, during, and/or after performing the HVLD inspection.

16. The method of claim 11, grounding the package using an additional grounding element comprising rollers, wherein the rollers are configured to retain and rotate the package.

17. A grounding system for use with a high voltage leak detection (HVLD) system configured to inspect a package using an inspection electrode and a detection, comprising: grounding elements comprising rollers configured to retain, rotate, and contact the package to remove, significantly reduce, or conduct away electric charge accumulation on the package, and
a movable grounding element that is configured to be moved by a controller to an operative position within a range of effective distance from a surface of the package between the inspection electrode and the detection electrode to ground the package.

18. The grounding system of claim 17, comprising an actuator configured to move the movable grounding element together with the inspection electrode and/or the detection electrode to ground the package.

19. The grounding system of claim 17, wherein the grounding elements are semi-conductive.

* * * * *